(12) United States Patent
Sum et al.

(10) Patent No.: US 7,812,008 B2
(45) Date of Patent: *Oct. 12, 2010

(54) 9-SUBSTITUTED TETRACYCLINES

(75) Inventors: Phaik-Eng Sum, Pomona, NY (US);
Tarek Mansour, New City, NY (US)

(73) Assignee: Wyeth LLC, Madison, NJ (US)

( * ) Notice: Subject to any disclaimer, the term of this patent is extended or adjusted under 35 U.S.C. 154(b) by 1093 days.

This patent is subject to a terminal disclaimer.

(21) Appl. No.: 11/354,306

(22) Filed: Feb. 14, 2006

(65) Prior Publication Data

US 2006/0183720 A1 Aug. 17, 2006

Related U.S. Application Data

(60) Provisional application No. 60/653,269, filed on Feb. 15, 2005.

(51) Int. Cl.
*A61K 31/65* (2006.01)
*C07C 237/26* (2006.01)

(52) U.S. Cl. .................... 514/152; 552/203
(58) Field of Classification Search ................. 514/152; 552/203

See application file for complete search history.

(56) References Cited

U.S. PATENT DOCUMENTS

| | | | |
|---|---|---|---|
| 2,482,055 A | 9/1949 | Duggar et al. |
| 3,007,965 A | 11/1961 | Growich, Jr. et al. |
| 3,043,875 A | 7/1962 | Beereboom et al. |
| 3,148,212 A | 9/1964 | Boothe et al. |
| 3,200,149 A | 8/1965 | Blackwood et al. |
| 3,226,436 A | 12/1965 | Petisi et al. |
| RE26,253 E | 8/1967 | Petisi et al. |
| 3,338,963 A | 8/1967 | Petisi et al. |
| 3,341,585 A | 9/1967 | Bitha et al. |
| 3,360,557 A | 12/1967 | Shu et al. |
| 3,360,561 A | 12/1967 | Zambrano et al. |
| 3,518,306 A | 6/1970 | Martell et al. |
| 5,021,407 A | 6/1991 | Levy |
| 5,494,903 A | 2/1996 | Hlavka et al. |
| 5,834,450 A | 11/1998 | Su |

FOREIGN PATENT DOCUMENTS

| | | | |
|---|---|---|---|
| EP | 0 582 788 A | | 2/1994 |
| EP | 0 582 829 A | | 2/1994 |
| EP | 582788 | * | 2/1994 |
| WO | WO 02/072532 A | | 9/2002 |

OTHER PUBLICATIONS

Sum, P.E., et al., Bioorganic & Medicinal Chemistry Letters, vol. 9, No. 10, pp. 1459-1462, 1999.
International Search Report, Jun. 11, 2006.
Richard C. Larock, Comprehensive Organic Transformations, pp. 411-415, 1989.
Chopra, Handbood of Experimental Pharmacology, vol. 78, pp 317-392, 1985.
Stuart B. Levy, et al., Antimicrobial Agents and Chemotherapy, vol. 33, No. 8, pp. 1373-1374, 1989.
A.A. Salyers, et al., Molecular Microbiology, vol. 4(1), pp 151-156, 1990.
Agnew, Chem. Int. Ed. Engl., vol. 25, pp. 508-524, 1986, John Stille.

* cited by examiner

*Primary Examiner*—Barbara P Badio
(74) *Attorney, Agent, or Firm*—Ram W. Sabnis

(57) ABSTRACT

This invention provides compounds of Formula (I);

I

[Chemical structure of tetracycline derivative with $R^1$, $R^2$, $R^3$ substituents, NH, OH, NH$_2$, and N(CH$_3$)$_2$ groups]

or a tautomer or pharmaceutically acceptable salts thereof useful as antibacterial agents.

11 Claims, No Drawings

9-SUBSTITUTED TETRACYCLINES

This application claims priority from copending provisional application No. 60/653,269, filed Feb. 15, 2005, the entire disclosure of which is hereby incorporated by reference.

FIELD OF THE INVENTION

The present invention relates to 9-substituted derivatives of tetracyclines which are useful as antimicrobial agents and exhibit antibacterial activity against a wide spectrum of organisms including organisms which are resistant to tetracyclines and other antibiotics.

BACKGROUND OF THE INVENTION

Since 1947 a variety of tetracycline antibiotics have been synthesized and described for the treatment of infectious diseases in man and animals. Tetracyclines inhibit protein synthesis by binding to the 30S subunit of the bacterial ribosome preventing binding of aminoacyl RNA (Chopra, Handbook of Experimental Pharmacology, Vol. 78, 317-392, Springer-Verlag, 1985). Resistance to tetracyclines has emerged among many clinically important microorganisms which limit the utility of these antibiotics. There are two major mechanisms of bacterial resistance to tetracyclines: a) energy-dependent efflux of the antibiotic mediated by proteins located in the cytoplasmic membrane which prevents intracellular accumulation of tetracycline (S. B. Levy, et al., Antimicrob. Agents Chemotherapy 33, 1373-1374 (1989); and b) ribosomal protection mediated by a cytoplasmic protein which interacts with the ribosome such that tetracycline no longer binds or inhibits protein synthesis (A. A. Salyers, B. S. Speers and N. B. Shoemaker, Mol. Microbiol, 4:151-156, 1990). The efflux mechanism of resistance is encoded by resistance determinants designated tetA-tetL. They are common in many Gram-negative bacteria (resistance genes Class A-E), such as Enterobacteriaceae, *Pseudomonas, Haemophilus* and *Aeromonas*, and in Gram-positive bacteria (resistance genes Class K and L), such as *Staphylococcus, Bacillus* and *Streptococcus*. The ribosomal protection mechanism of resistance is encoded by resistance determinants designated TetM, N and O, and is common in *Staphylococcus, Streptococcus, Campylobacter, Gardnerella, Haemophilus* and *Mycoplasma* (A. A. Salyers, B. S. Speers and N. B. Shoemaker, Mol. Microbiol, 4:151-156 1990).

A particularly useful tetracycline compound is 7-(dimethylamino)-6-demethyl-6-deoxytetracycline, known as minocycline (see U.S. Pat. No. 3,148,212, U.S. Pat. No. RE 26,253 and U.S. Pat. No. 3,226,436 discussed below). However, strains harboring the tetB (efflux in gram-negative bacteria) mechanism, but not tetK (efflux in *Staphylococcus*) are resistant to minocycline. Also, strains carrying tetM (ribosomal protection) are resistant to minocycline. This invention describes the synthesis of novel tetracycline compounds which demonstrate significant in vitro and in vivo activity vs. tetracycline and minocycline susceptible strains and some tetracycline and minocycline resistant strains, that is, those harboring the tetM (ribosomal protection) resistance determinants.

Duggar, U.S. Pat. No. 2,482,055, discloses the preparation of Aureomycin® by fermentation which have antibacterial activity. Growich et al., U.S. Pat. No. 3,007,965, disclose improvements to the fermentation preparation. Beereboom et al., U.S. Pat. No. 3,043,875 discloses tetracycline derivatives Boothe et al., U.S. Pat. No. 3,148,212, reissued as U.S. Pat. No. RE 26,253, and Petisi et al., U.S. Pat. No. 3,226,436, discloses tetracycline derivatives which are useful for treating bacterial infections. Blackwood et al., U.S. Pat. No. 3,200,149 discloses tetracycline derivatives which possess microbiological activity. Petisi et al., U.S. Pat. No. 3,338,963 discloses tetracycline compounds which have broad-spectrum antibacterial activity. Bitha et al., U.S. Pat. No. 3,341,585 discloses tetracycline compounds which have broad-spectrum antibacterial activity. Shu, U.S. Pat. No. 3,360,557 discloses 9-hydroxytetracyclines which have been found to possess antibacterial activity. Zambrano, U.S. Pat. No. 3,360,561 discloses a process for preparing 9-nitrotetracyclines. Martell et al., U.S. Pat. No. 3,518,306 discloses tetracyclines which possess in vivo antibacterial activity.

In U.S. Pat. No. 5,021,407 a method of overcoming the resistance of tetracycline resistant bacteria is disclosed. The method involves utilizing a blocking agent compound in conjunction with a tetracycline type antibiotic. This patent does not disclose novel tetracycline compounds which themselves have activity against resistant organisms. Described in U.S. Pat. No. 5,494,903 are 7-substituted-9-substitutedamino-6-demethyl-6-deoxytetracyclines which have broad spectrum antibacterial activity.

In summary, none of the above patents teach or suggest the novel compounds of this application.

SUMMARY OF THE INVENTION

In accordance with the present invention, there is provided compounds represented by Formula (I);

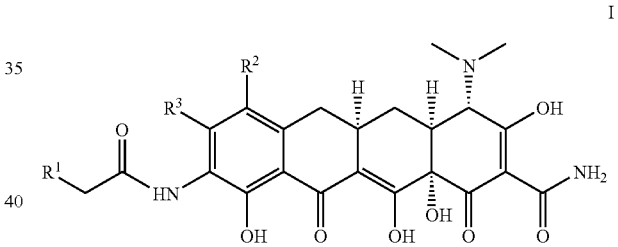

wherein:
R$^1$ is a moiety selected from the group:

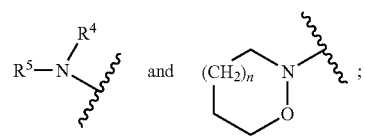

n is an integer of 1 or 2;

R$^2$ is selected from hydrogen, amino, —NR$^6$R$^7$, alkyl of 1 to 12 carbon atoms optionally substituted, aryl of 6, 10 or 14 carbon atoms optionally substituted, alkenyl of 2 to 12 carbon atoms optionally substituted, alkynyl of 2 to 12 carbon atoms optionally substituted, halogen, and a 5 to 10 membered heteroaryl ring optionally substituted, having 1 to 4 heteroatoms independently selected from N, O and S;

R$^3$ is selected from hydrogen, alkyl of 1 to 12 carbon atoms optionally substituted, aryl of 6, 10 or 14 carbon atoms optionally substituted, alkenyl of 2 to 12 carbon atoms optionally substituted, vinyl, alkynyl of 2 to 12 carbon atoms optionally substituted and halogen;

$R^4$ is H, alkyl of 1 to 12 carbon atoms optionally substituted, cycloalkyl of 3 to 8 carbon atoms, bicycloalkyl of 5 to 10 carbon atoms or aralkyl optionally substituted;

$R^5$ is OH or —$OR^8$;

$R^6$ and $R^7$ are each independently H or alkyl of 1 to 12 carbon atoms or when optionally taken together with the nitrogen atom to which each is attached form a 3 to 8 membered saturated heterocyclyl ring;

$R^8$ is alkyl of 1 to 12 carbon atoms optionally substituted; or a tautomer or pharmaceutically acceptable salts thereof.

DEFINITIONS

The term alkyl means a straight or branched alkyl moiety of 1 to 12 carbon atoms optionally independently substituted with 1 to 3 substituents selected from the group halogen, amino, cyano, cycloalkyl of 3 to 6 carbon atoms, aryl optionally substituted as discussed below, phenyl, hydroxyl, alkoxy of 1 to 12 carbon atoms, N-alkyl of 1 to 12 carbon atoms, N-(alkyl of 1 to 12 carbon atoms)$_2$, N-cycloalkyl of 3 to 6 carbon atoms, N-(alkyl of 1 to 12 carbon atoms)-aryl optionally substituted and a 3 to 8 membered heterocyclyl ring containing 1 to 4 heteroatoms independently selected from N, O and S. In some embodiments of the invention alkyl is a moiety of 1 to 6 carbon atoms optionally substituted with 1 to 3 substituents selected from those defined above. In other embodiments of the invention alkyl is a moiety of 1 to 3 carbon atoms optionally substituted with 1 or 2 substituents selected from those defined above.

The term alkenyl means a straight or branched carbon chain of 2 to 12 carbon atoms having at least one site of unsaturation optionally independently substituted with 1 to 3 substituents selected from the group aryl, phenyl, heteroaryl, halogen, amino, cyano, hydroxyl, and alkoxy of 1 to 12 carbon atoms. Examples of alkenyl include, but are not limited to, vinyl and propenyl.

As used herein the term alkynyl includes both straight chain and branched moieties containing 2 to 12 carbon atoms having at least one carbon to carbon triple bond optionally substituted with 1 to 3 substituents independently selected from the group halogen, amino, cyano, hydroxyl, and alkoxy of 1 to 12 carbon atoms.

As used herein the term alkoxy refers to alkyl-O— wherein alkyl is hereinbefore defined.

As used herein the term aryl means an aromatic moiety having 6 to 14 carbon atoms preferably 6 to 10 carbon atoms, optionally substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, and phenyl. In particular, aryl is preferably phenyl or naphthyl optionally substituted with 1 to 3 substituents as defined herein above.

The term aralkyl as used herein of 7 to 16 carbon atoms means an alkyl substituted with an aryl group in which the aryl and alkyl group are previously defined. Non-limiting exemplary aralkyl groups include benzyl and phenethyl and the like optionally substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, and phenyl.

As used herein, haloalkyl refers to an alkyl as hereinbefore defined, independently substituted with 1 to 3, F, Cl or Br.

As used herein the term bicycloalkyl means a hydrocarbon radical containing 5 to 10 carbon atoms which is saturated or partially unsaturated.

As used herein the term halogen or halo means F, Cl, Br or I. In some embodiments of the invention, halo is Cl or Br.

As used herein the term cycloalkyl means a saturated monocyclic ring having from 3 to 6 carbon atoms. Exemplary cycloalkyl rings include but are not limited to cyclopropyl, cyclobutyl, cyclopentyl, and cyclohexyl. In an embodiment of the invention cycloalkyl is a moiety of 5 or 6 carbon atoms.

The term heteroaryl means a 5 to 10 membered aromatic monocyclic or bicyclic heterocyclic aromatic ring having from 1 to 4 ring members independently selected from O, N and S. Monocyclic heterocyclic aromatic rings preferably have 5 to 6 ring atoms and bicyclic rings preferably have 8 to 10 membered ring structures containing 1 to 4 heteroatoms independently selected from O, N and S. Heteroaryl rings may optionally be substituted with 1 to 3 substitutents selected from the group halogen, cyano, nitro, hydroxy, amino, alkylamino, dialkylamino, alkoxy, aryloxy, —$CH_2OCOCH_3$ and carboxy. Non-limiting heteroaryl moieties optionally substituted include: furanyl, thienyl, pyridinyl, tetrazolyl, imidazo, thiazolyl, benzofuranyl, benzothienyl, and quinolinyl and the like.

The term heterocyclyl as used herein represents a saturated or partially saturated 3 to 8 membered ring containing 1 to 4 heteroatoms independently selected from N, O and S. Representative examples are pyrrolidyl, piperidyl, piperazinyl, morpholinyl, thiomorpholinyl, aziridinyl, tetrahydrofuranyl and the like.

Some of the compounds of formula (I) may also exist in their tautomeric forms. Such forms although not explicitly indicated in the above formula are intended to be included within the scope of the present invention. For instance, compounds of formula (I) which exist as tautomers are depicted below:

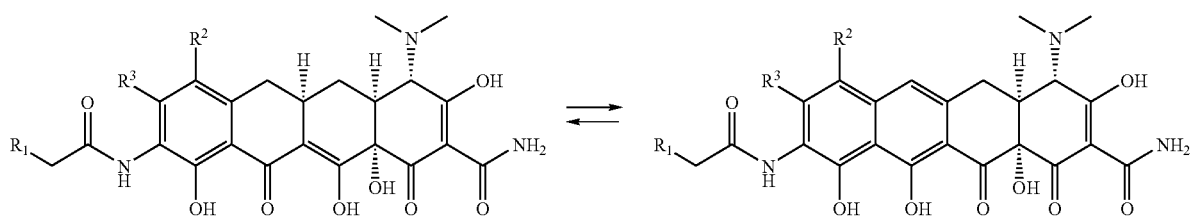

In one embodiment of this invention, $R^1$ of Formula (I) is a moiety $R^4R^5N—$, wherein $R^4$ is alkyl and $R^5$ is OH.

In an additional embodiment of this invention, $R^1$ of Formula (I) is a moiety $R^4R^5N—$, wherein $R^4$ is cycloalkyl and $R^5$ is OH.

In an additional embodiment of this invention, $R^1$ of Formula (I) is a moiety $R^4R^5N—$, wherein $R^5$ is alkoxy and $R^4$ is alkyl.

In an additional embodiment of this invention, $R^1$ of Formula (I) is a moiety $R^4R^5N—$, wherein $R^5$ is alkoxy and $R^4$ is H.

In a further embodiment of this invention, $R^1$ of Formula (I) is a moiety $R^4R^5N—$, wherein $R^4$ is aralkyl and $R^5$ is OH.

Another embodiment of the invention is where $R^1$ of Formula (I) is a moiety of the formula

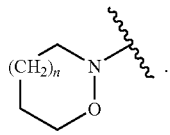

A preferred embodiment of the invention is where n is 1 and $R^1$ of Formula (I) is a moiety

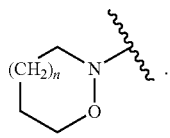

A preferred embodiment of the invention is where n is 1 and $R^2$ of Formula (I) is heteroaryl of 5 or 6 ring atoms.

In one embodiment of this invention, $R^2$ of Formula (I) is furanyl.

In another embodiment of this invention, $R^2$ of Formula (I) is thienyl.

In a further embodiment of this invention, $R^2$ of Formula (I) is pyridinyl.

In some embodiments of the invention $R^6$ and $R^7$ are both methyl.

$R^3$ is suitably hydrogen. $R^2$ is suitably dimethylamino. $R^4$ is suitably OH or $OR^8$ wherein $R^8$ is an unsubstituted alkyl of 1 to 3 carbon atoms. $R^4$ is suitably hydrogen, an unsubstituted alkyl of 1 to 3 carbon atoms, an unsubstituted alkoxy of 1 to 3 carbon atoms, cyclohexyl or benzyl.

Preferred compounds of the invention include:
(4S,4aS,5aR,12aS)-9-{[N-(tert-butyl)-N-hydroxyglycyl]amino}-4,7-bis(dimethylamino)-3,10,12,12a-tetrahydroxy-1,11-dioxo-1,4,4a,5,5a,6,11,12a-octahydrotetracene-2-carboxamide;
(4S,4aS,5aR,12aS)-9-[(N-cyclohexyl-N-hydroxyglycyl)amino]-4,7-bis(dimethylamino)-3,10,12,12a-tetrahydroxy-1,11-dioxo-1,4,4a,5,5a,6,11,12a-octahydrotetracene-2-carboxamide;
(4S,4aS,5aR,12aS)-4,7-bis(dimethylamino)-3,10,12,12a-tetrahydroxy-9-[(N-hydroxy-N-isopropylglycyl)amino]-1,11-dioxo-1,4,4a,5,5a,6,11,12a-octahydrotetracene-2-carboxamide;
(4S,4aS,5aR,12aS)-4,7-bis(dimethylamino)-3,10,12,12a-tetrahydroxy-9-[(1,2-oxazinan-2-ylacetyl)amino]-1,11-dioxo-1,4,4a,5,5a,6,11,12a-octahydrotetracene-2-carboxamide;
(4S,4aS,5aR,12aS)-9-[(N-benzyl-N-hydroxyglycyl)amino]-4,7-bis(dimethylamino)-3,10,12,12a-tetrahydroxy-1,11-dioxo-1,4,4a,5,5a,6,11,12a-octahydrotetracene-2-carboxamide;
(4S,4aS,5aR,12aS)-4,7-bis(dimethylamino)-3,10,12,12a-tetrahydroxy-9-[(N-methoxy-N-methylglycyl)amino]-1,11-dioxo-1,4,4a,5,5a,6,11,12a-octahydrotetracene-2-carboxamide;
(4S,4aS,5aR,12aS)-9-{[N-(tert-butoxy)glycyl]amino}-4,7-bis(dimethylamino)-3,10,12,12a-tetrahydroxy-1,11-dioxo-1,4,4a,5,5a,6,11,12a-octahydrotetracene-2-carboxamide;
(4S,4aS,5aR,12aS)-4,7-bis(dimethylamino)-3,10,12,12a-tetrahydroxy-9-[(N-methoxyglycyl)amino]-1,11-dioxo-1,4,4a,5,5a,6,11,12a-octahydrotetracene-2-carboxamide;
(4S,4aS,5aR,12aS)-4-(dimethylamino)-3,10,12,12a-tetrahydroxy-7-iodo-9-[(1,2-oxazinan-2-ylacetyl)amino]-1,11-dioxo-1,4,4a,5,5a,6,11,12a-octahydrotetracene-2-carboxamide; and
(4S,4aS,5aR,12aS)-4-(dimethylamino)-3,10,12,12a-tetrahydroxy-9-[(1,2-oxazinan-2-ylacetyl)amino]-1,11-dioxo-7-thien-2-yl-1,4,4a,5,5a,6,11,12a-octahydrotetracene-2-carboxamide.

DESCRIPTION OF THE PREFERRED EMBODIMENTS

The novel compounds of the present invention may be readily prepared in accordance with the following Schemes 1 and 2.

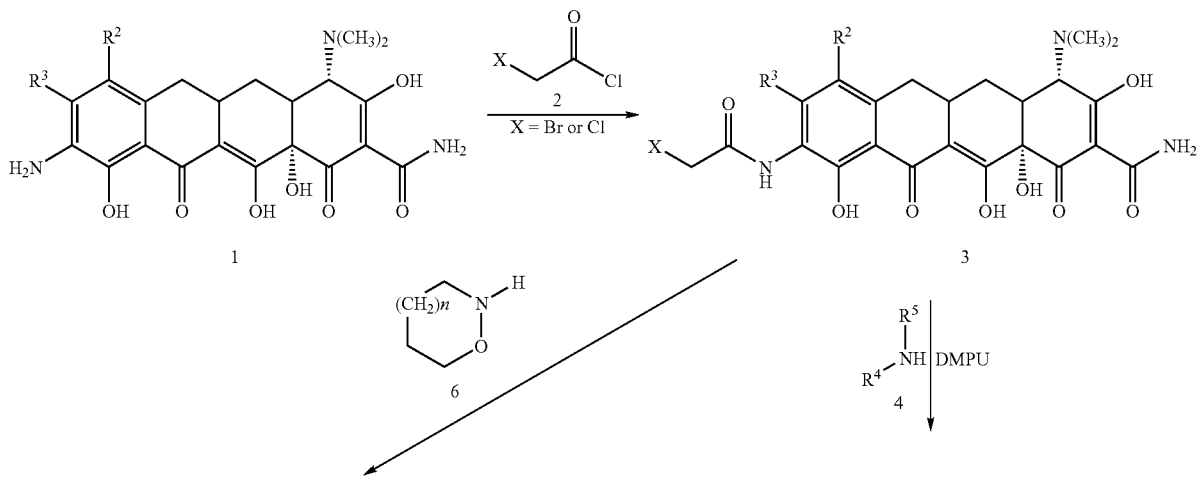

Scheme 1

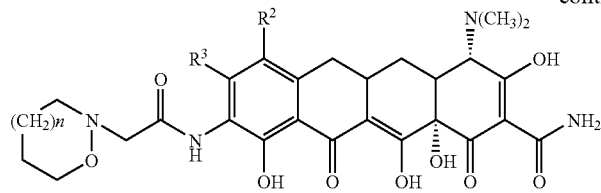

7

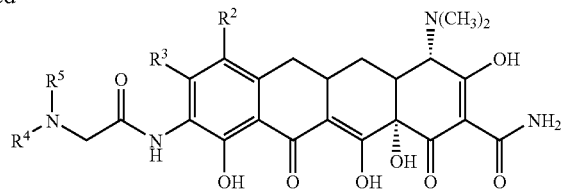

5

As described in Scheme 1, 9-amino-7-substituted-8-substituted-6-demethyl-6-deoxytetracyclines 1 where $R^2$ and $R^3$ are hereinbefore defined are reacted with excess haloacetyl bromide or chloride 2, optionally in the presence of an inorganic or organic base, to afford haloacetyltetracycline 3. Inorganic bases include sodium bicarbonate, sodium carbonate, potassium carbonate, sodium acetate, sodium hydrogencarbonate, and the like. Organic bases include pyridine, N,N-diethyl isopropylamine, triethylamine and the like. Haloacetyltetracycline 3 is further reacted with amine 4 where $R^4$ and $R^5$ are hereinbefore defined, optionally in the presence of an inorganic or organic base if amine 4 is an acid salt, in aprotic solvents which include 1,3-dimethyl-3,4,5,6-tetrahydro-2(1H)-pyrimidinone (DMPU)/acetonitrile or other optional solvents which further include water-tetrahydrofuran, N-methylpyrrolidone, or N,N-dimethylformamide to afford 9-(N-substituted-N-substitutedglycyl) tetracyclines 5 where $R^2$, $R^3$, $R^4$ and $R^5$ are hereinbefore defined. Reaction of haloacetyltetracycline 3 with cyclicamine 6 gives 9-substituted-tetracycline 7.

Scheme 2

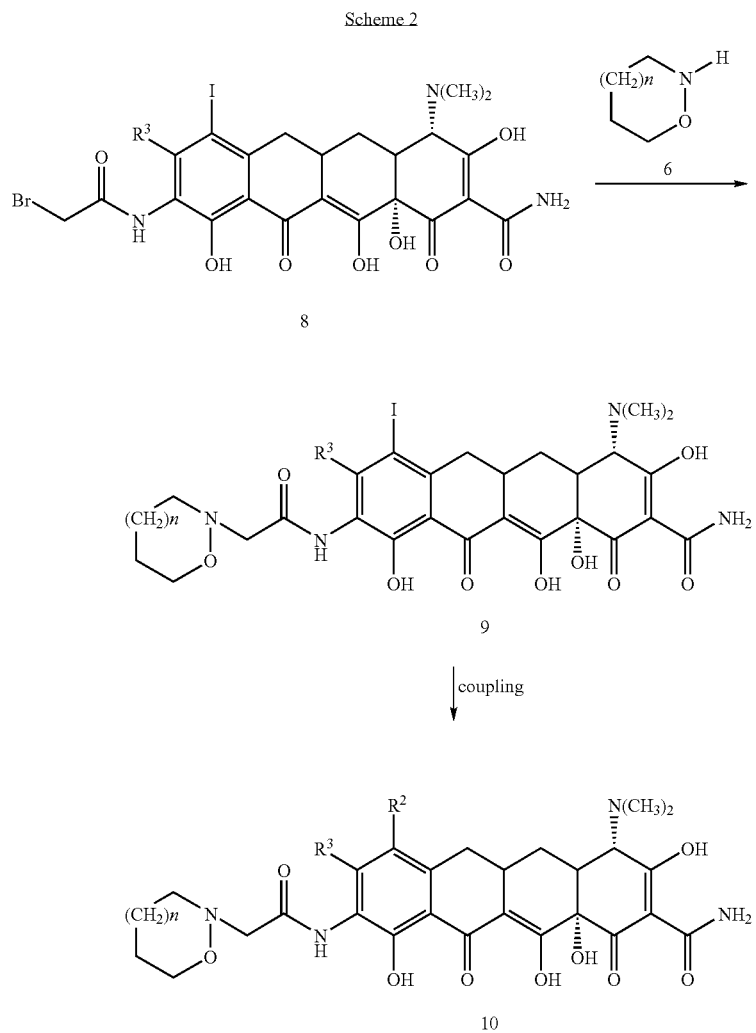

As shown in Scheme 2, haloacetyltetracycline 8 is reacted with excess cyclicamine 6 in aprotic solvents which include 1,3-dimethyl-3,4,5,6-tetrahydro-2(1H)-pyrimidinone (DMPU)/acetonitrile or other optional solvents which further include water-tetrahydrofuran, N-methylpyrrolidone, or DMF to afford intermediate tetracycline 9. Coupling of intermediate tetracycline 9 using palladium coupling in the presence of dichlorobis(triphenylphosphine)palladium(II), triphenylarsine, copper (I) iodide and (tributylstannyl)-$R^2$, where $R^2$ is thienyl, furanyl or pyridinyl affords 9-substituted-tetracycline 10 using general methods as described in (Angew. Chem. Int. Ed. Engl. 25 (1986) 508-524).

Reactions are performed in a solvent appropriate to the reagents and materials employed and suitable for the transformation being effected. It is understood by those skilled in the art of organic synthesis that the various functionalities present on the molecule must be consistent with the chemical transformations proposed. This may necessitate judgement as to the order of synthetic steps, protecting groups, if required, and deprotection conditions. Substituents on the starting materials may be incompatible with some of the reaction conditions. Such restrictions to the substituents which are compatible with the reaction conditions will be apparent to one skilled in the art.

Some of the compounds of the hereinbefore described schemes have center of asymmetry. The compounds may, therefore, exist in at least two and often more stereoisomeric forms. The present invention encompasses all stereoisomers of the compounds whether free from other stereoisomers or admixed with other stereoisomers in any proportion and thus includes, for instance, a racemic mixture of enantiomers as well as the diastereomeric mixture of isomers. The absolute configuration of any compound may be determined by conventional X-ray crystallography.

The compounds of the invention may be obtained as metal complexes such as aluminum, calcium, iron, magnesium, manganese and complex salts; inorganic and organic salts and corresponding Mannich base adducts using methods known to those skilled in the art (Richard C. Larock, Comprehensive Organic Transformations, VCH Publishers, 411-415, 1989). Preferably, the compounds of the invention are obtained as inorganic salts such as hydrochloric, hydrobromic, hydroiodic, phosphoric, nitric or sulfate; or organic salts such as acetate, benzoate, citrate, cysteine or other amino acids, fumarate, glycolate, maleate, succinate, tartrate alkylsulfonate or arylsulfonate. In all cases, the salt formation occurs with the C(4)-dimethylamino group. The salts are preferred for oral and parenteral administration.

Standard Pharmacological Test Procedures

Methods for in Vitro Antibacterial Evaluation
The minimum inhibitory concentration (MIC)
Antimicrobial susceptibility testing. The in vitro activities of representative examples of antibiotics of the invention are determined by the broth microdilution method as recommended by the National Committee for Clinical Laboratory Standards (NCCLS) (1). Mueller-Hinton II broth (MHBII) (BBL Cockeysville, Md.) is the medium employed in the testing procedures. Microtiter plates containing serial dilutions of each antimicrobial agent are inoculated with each organism to yield the appropriate density ($10^5$ CFU/ml) in a 100 μl final volume. The plates are incubated for 18-22 hours at 35° C. in ambient air. The minimal inhibitory concentration for all isolates is defined as the lowest concentration of antimicrobial agent that completely inhibits the growth of the organism as detected by the unaided eye. Results are displayed in Table 1.
1. NCCLS. 2000. Methods for Dilution Antimicrobial Susceptibility Tests for Bacteria That Grow Aerobically; Approved Standards: M7-A5, vol. 20. National Committe for Clinical Laboratory Standards, Wayne, Pa.

TABLE 1

|  | Growth Control | Control Minocycline | Example 1 | Example 2 | Example 3 | Example 4 | Example 5 |
|---|---|---|---|---|---|---|---|
| E. coli GC2270 (tet(M)) | >64 | 64 | 8 | 4 | >64 | 8 | 4 |
| E. coli GC4559 (parent GC4560) | >64 | 2 | 8 | 8 | >64 | 16 | 4 |
| E. coli GC4560 (IMP mutant) | >64 | <0.06 | 0.25 | 0.25 | 1 | 0.50 | 0.25 |
| E. coli GC2203 (ATCC Control) | >64 | 0.50 | 2 | 2 | 32 | 8 | 2 |
| E. coli GC1073 (tet(B)) | >64 | 16 | 16 | 16 | >64 | 16 | 4 |
| S. aureus GC1131 (Clinical) | >64 | 0.12 | 4 | 4 | 4 | 1 | 1 |
| S. aureus GC6466 (tet(M)) | >64 | 8 | 8 | 4 | 4 | 1 | 1 |
| S. aureus GC6467 (tet(M) + (K)) | >64 | 8 | >64 | 16 | 16 | >64 | 4 |
| S. aureus GC1079 (tet(K)) | >64 | 0.12 | 16 | 8 | 8 | 16 | 2 |
| S. aureus GC4536 (Smith MP -In Vivo) | >64 | 0.25 | 4 | 4 | 4 | 1 | 1 |
| S. aureus GC2216 (ATCC Control) | >64 | 0.12 | 4 | 2 | 4 | 1 | 1 |
| E. faecalis GC4555 (ATCC Control) | >64 | 4 | 1 | 1 | 4 | 1 | 1 |
| E. faecalis GC2267 (tet(L) + (M) + (S)) | >64 | 16 | 16 | 4 | 8 | 8 | 4 |
| E. faecalis GC2242 (Van-resistant) | >64 | 8 | 2 | 2 | 8 | 1 | 2 |
| S. pneumoniae* GC4465 (Clinical) | >64 | <0.06 | 0.25 | 0.25 | 1 | 0.25 | 0.12 |
| S. pneumoniae* GC1894 (Clinical) | >64 | 4 | 0.25 | 0.25 | 1 | 0.25 | 0.25 |
| S. pyogenes* GC4563 (Clinical) | >64 | <0.06 | 0.12 | 0.25 | 0.50 | 0.12 | 0.25 |
| M. catarrhalis* GC6907 (Clinical) | >64 | <0.06 | 0.50 | 1 | 2 | 0.50 | 0.25 |
| H. influenzae<> GC6896 (ATCC Control) | >64 | 0.25 | 2 | 2 | 8 | 2 | 2 |
| C. albicans GC3066 ATCC (Control) | >64 | >64 | >64 | >64 | >64 | >64 | >64 |

|  | Control Minocycline | Example 6 | Example 7 | Example 8 | Example 9 | Example 10 |
|---|---|---|---|---|---|---|
| E. coli GC2270 (tet(M)) | 64 | 16 | >64 | >64 | >64 | >64 |
| E. coli GC4559 (parent GC4560) | 2 | 8 | >64 | >64 | >64 | >64 |
| E. coli GC4560 (IMP mutant) | 0.25 | 0.25 | 1 | 2 | 2 | 4 |
| E. coli GC2203 (ATCC Control) | 1 | 16 | >64 | >64 | >64 | >64 |
| E. coli GC1073 (tet(B)) | 16 | 32 | >64 | >64 | >64 | >64 |
| S. aureus GC1131 (Clinical) | 0.50 | 4 | 4 | 4 | 2 | 4 |

TABLE 1-continued

| | | | | | | |
|---|---|---|---|---|---|---|
| S. aureus GC6466 (tet(M)) | 8 | 2 | 2 | 2 | 1 | 2 |
| S. aureus GC6467 (tet(M) + (K)) | 16 | 64 | >64 | 64 | 4 | 8 |
| S. aureus GC1079 (tet(K)) | 1 | 8 | 32 | 16 | 2 | 4 |
| S. aureus GC4536 (Smith MP -In Vivo) | 1 | 2 | 2 | 2 | 4 | 4 |
| S. aureus GC2216 (ATCC Control) | 0.25 | 2 | 2 | 2 | 1 | 4 |
| E. faecalis GC4555 (ATCC Control) | 4 | 1 | 1 | 2 | 4 | 8 |
| E. faecalis GC2267 (tet(L) + (M) + (S)) | 16 | 8 | 8 | 8 | 2 | 4 |
| E. faecalis GC2242 (Van-resistant) | 16 | 2 | 2 | 2 | 8 | 4 |
| S. pneumoniae* GC4465 (Clinical) | 0.12 | 0.12 | 0.50 | 1 | 1 | 2 |
| S. pneumoniae* GC1894 (Clinical) | 4 | 0.25 | 0.50 | 0.50 | 0.50 | 2 |
| S. pyogenes* GC4563 (Clinical) | <0.06 | 0.25 | 0.25 | 1 | 1 | 2 |
| M. catarrhalis* GC6907 (Clinical) | <0.06 | 0.50 | 0.50 | 1 | 2 | 2 |
| H. influenzae<> GC6896 (ATCC Control) | 1 | 2 | 4 | 64 | >64 | >64 |
| C. albicans GC3066 ATCC (Control) | >64 | >64 | >64 | >64 | >64 | >64 |

In Vivo Antibacterial Evaluation: The therapeutic effects of representative examples of the invention are determined against acute lethal infection with *Staphylococcal aureus* Smith M P, Female mice, strain CD-1 (Charles River Laboratoties), ca. 20 grams, are challenged by an intraperitoneal injection of sufficient bacteria (suspended in broth or hog mucin) to kill non-treated controls within 24-28 hours. Antibacterial agents, contained in 0.5 ml of 0.2% aqueous agar, are administered subcutaneously or orally 30 minutes after injection. When an oral dosing schedule is used, animal are deprived of food for 5 hours before and 2 hours after injection. Five mice are treated at each dose level. The 7 day survival ratios from 3 separate tests are pooled for calculation of median effective dose (ED50). Results are displayed in Table 2.

TABLE 2

| Example No. | Structure R¹ | SOD* ED$_{50}$ (mg/kg) | MIC μg/ml | SIV* ED$_{50}$ (mg/kg) |
|---|---|---|---|---|
| Minocyoline | | 0.6-0.93 | 0.25 | 0.37-0.42 |
| GAR-936 | tert-butyl-NH-CH₂-C(O)-NH- | 36 | 0.25 | 0.46 |
| 1 | cyclohexyl-N(OH)-CH₂-C(O)-NH- | 7.75 | 1 | 1.56 |
| 2 | isopropyl-N(OH)-CH₂-C(O)-NH- | 18 | 1 | 0.25-0.5 |
| 3 | tert-butyl-N(OH)-CH₂-C(O)-NH- | >32 | 1 | 2-4 |

TABLE 2-continued

[Core structure: tetracycline scaffold with R¹-CH2-C(O)-NH- substituent]

| Example No. | Structure R¹-C(O)-NH-CH2- | SOD* ED$_{50}$ (mg/kg) | MIC μg/ml | SIV* ED$_{50}$ (mg/kg) |
|---|---|---|---|---|
| 4 | tBu-O-NH-CH2-C(O)-NH- | 1.1 | 4 | 0.25-1.0 |
| 5 | MeO-NH-CH2-C(O)-NH- | 16-32 | 1 | 0.5-1 |
| 6 | Ph-CH2-N(OH)-CH2-C(O)-NH- | >16 | 2 | >4 |
| 7 | MeO-N(Me)-CH2-C(O)-NH- | 16-32 | 2 | 0.5-2 |
| 8 | (tetrahydro-1,2-oxazin-2-yl)-CH2-C(O)-NH- | 3.59 | 2 | 0.56 |

*Single oral dose; SOD and SIV: single intravenous dose

When the compounds of the invention are employed as antibacterials, they can be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

An effective amount of compound from 2.0 mg/kg of body weight to 100.0 mg/kg of body weight may be administered one to five times per day via any typical route of administration including but not limited to oral, parenteral (including subcutaneous, intravenous, intramuscular, intrasternal injection or infusion techniques), topical or rectal, in dosage unit formulations containing conventional non-toxic pharmaceutically acceptable carriers, adjuvants and vehicles. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred. These active compounds may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacterial and fungi. The carrier can be a solvent or dispersion medium containing, for example, water, ethanol, polyol (e.g., glycerol, propylene glycol and liquid polyethylene glycol), suitable mixtures thereof, and vegetable oil.

The invention will be more fully described in conjunction with the following specific examples which are not to be construed as limiting the scope of the invention.

Example 1

(4S,4aS,5aR,12aS)-9-[(N-cyclohexyl-N-hydroxyglycyl)amino]-4,7-bis(dimethylamino)-3,10,12,12a-tetrahydroxy-1,11-dioxo-1,4,4a,5,5a,6,11,12a-octahydrotetracene-2-carboxamide

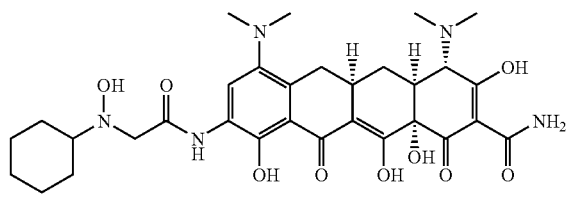

N-cyclohexylhydroxylamine hydrochloride (1.5 g) and sodium carbonate (1.5 g) in dichloromethane is stirred at room temperature for 24 hour, filtered and the filtrate concentrated at reduced pressure to a residue. The residue as the free amine is then redissolved in mixture of acetonitrile and DMPU (3 ml/15 ml) and 0.5 g of 9-(2-bromo-acetylamino)-4,7-bis-dimethylamino-3,10,12,12a-tetrahydroxy-1,11-dioxo-1,4,4a,5,5a,6,11,12a-octahydro-naphthacene-2-carboxylic acid amide is added. The reaction mixture is stirred at room temperature for 2 hr. and then poured into mixture of ether and isopropanol and the product collected by filtration. The product is redissolved in water and extracted with dichloromethane at a pH between 3-7. The dichloromethane is separated and evaporated to afford the product as residue.

MS (ESI) m/z 628.46 (M+H);
MS (ESI) m/z 314.75 (M+2H);
HRMS: calcd for $C_{31}H_{41}N_5O_9 \cdot HCl$, 663.2671; found (ESI+), 628.29728;

The compounds of this invention listed below in Examples 2 to 37 are prepared substantially following the method described in detail hereinabove in Example 1.

Example 2

(4S,4aS,5aR,12aS)-4,7-bis(dimethylamino)-3,10,12,12a-tetrahydroxy-9-[(N-hydroxy-N-isopropylglycyl)amino]-1,11-dioxo-1,4,4a,5,5a,6,11,12a-octahydrotetracene-2-carboxamide

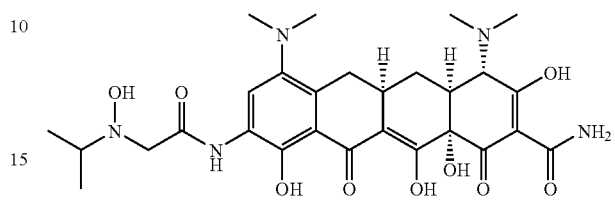

The compound of the example is prepared by the procedure of Example 1 using 1.0 g of N-isopropylhydroxyamine, 1 g of sodium carbonate, and 0.25 g of 9-(2-bromo-acetylamino)-4,7-bis-dimethylamino-3,10,12,12a-tetrahydroxy-1,11-dioxo-1,4,4a,5,5a,6,11,12a-octahydro-naphthacene-2-carboxylic acid amide in 8 ml DMPU and 2.5 ml acetonitrile to give 0.066 g of the product.

MS (ESI) m/z 588.3 (M+H);
MS (ESI) m/z 294.6 (M+2H);
HRMS: calcd for $C_{28}H_{37}N_5O_9 \cdot HCl$, 623.2358; found (ESI−), 586.25116;
MS (ESI) m/z 588.3 (M+H);
MS (ESI) m/z 294.7 (M+2H);
MS (ESI) m/z 315.3 (M+ACN+2H);
HRMS: calcd for $C_{28}H_{37}N_5O_9 \cdot HCl$, 623.2358; found (ESI+), 588.26705;

Example 3

(4S,4aS,5aR,12aS)-9-{[N-(tert-butyl)-N-hydroxyglycyl]amino}-4,7-bis(dimethylamino)-3,10,12,12a-tetrahydroxy-1,11-dioxo-1,4,4a,5,5a,6,11,12a-octahydrotetracene-2-carboxamide

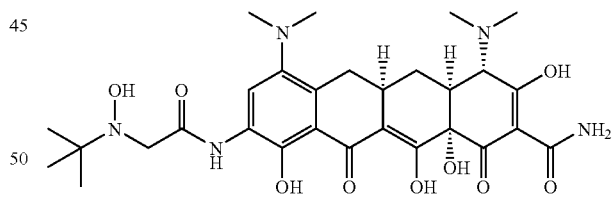

The compound of the example is prepared by the procedure of Example 1 using 1.5 g of N-tert-butyllhydroxyamine, 2 g of sodium carbonate, and 0.505 g of 9-(2-bromo-acetylamino)-4,7-bis-dimethylamino-3,10,12,12a-tetrahydroxy-1,11-dioxo-1,4,4a,5,5a,6,11,12a-octahydro-naphthacene-2-carboxylic acid amide in 8 ml DMPU and 2.5 ml acetonitrile to give 0.066 g of the product.

MS (ESI) m/z 602.44 (M+H);
MS (ESI) m/z 301.75 (M+2H);
MS (ESI) m/z 602.3 (M+H);
MS (ESI) m/z 301.8 (M+2H);
MS (ESI) m/z 322.2 (M+ACN+2H);
HRMS: calcd for $C_{29}H_{39}N_5O_9 \cdot HCl$, 637.2515; found (ESI+), 602.28268;

Example 4

(4S,4aS,5aR,12aS)-9-{[N-(tert-butoxy)glycyl]amino}-4,7-bis(dimethylamino)-3,10,12,12a-tetrahydroxy-1,11-dioxo-1,4,4a,5,5a,6,11,12a-octahydrotetracene-2-carboxamide

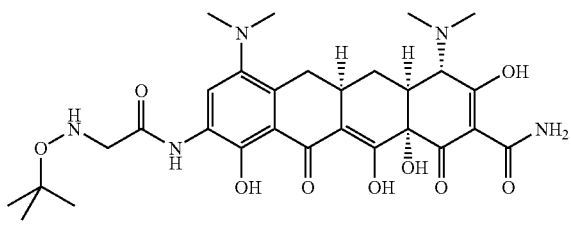

The compound of the example is prepared by the procedure of Example 1 using 1.5 g of O-tert-butyllhydroxyamine, (neutralized by NaOH, extracted with methylene chloride) and 0.5 of 9-(2-bromo-acetylamino)-4,7-bis-dimethylamino-3,10,12,12a-tetrahydroxy-1,11-dioxo-1,4,4a,5,5a,6,11,12a-octahydro-naphthacene-2-carboxylic acid amide in 6 ml DMPU and 2.5 ml acetonitrile to give 0.12 g of the product.

MS (ESI) m/z 602.3 (M+H);
MS (ESI) m/z 301.9 (M+2H);
MS (ESI) m/z 322.3 (M+ACN+2H);
HRMS: calcd for $C_{29}H_{39}N_5O_9 \cdot HCl$, 637.2515; found (ESI+), 602.28126;

Example 5

(4S,4aS,5aR,12aS)-4,7-bis(dimethylamino)-3,10,12,12a-tetrahydroxy-9-[(N-methoxyglycyl)amino]-1,11-dioxo-1,4,4a,5,5a,6,11,12a-octahydrotetracene-2-carboxamide

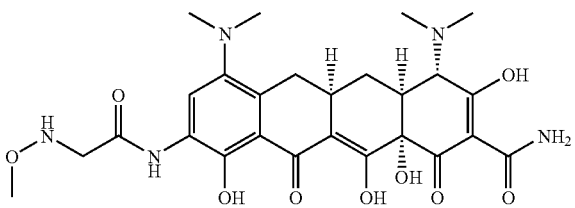

The compound of the example is prepared by the procedure of example 1 using 1.5 g of methoxyamine hydrochloride (neutralized by NaOH, extracted with methylene chloride), and 0.5 g of 9-(2-bromo-acetylamino)-4,7-bis-dimethylamino-3,10,12,12a-tetrahydroxy-1,11-dioxo-1,4,4a,5,5a,6,11,12a-octahydro-naphthacene-2-carboxylic acid amide in 8 ml DMPU and 2.5 ml acetonitrile to give 0.1 g of the product.

MS (ESI) m/z 560.2 (M+H);
MS (ESI) m/z 280.9 (M+2H);
HRMS: calcd for $C_{26}H_{33}N_5O_9 \cdot HCl$, 595.2045; found (ESI+), 560.23314;

Example 6

(4S,4aS,5aR,12aS)-9-[(N-benzyl-N-hydroxyglycyl)amino]-4,7-bis(dimethylamino)-3,10,12,12a-tetrahydroxy-1,11-dioxo-1,4,4a,5,5a,6,11,12a-octahydrotetracene-2-carboxamide

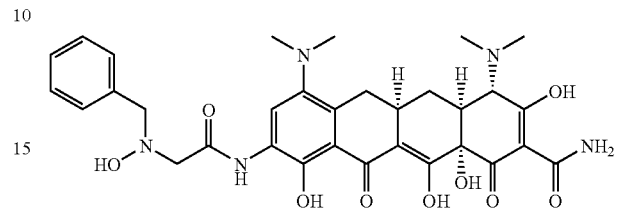

The compound of the example is prepared by the procedure of Example 1 using 3 g of N-benzylhydroxylamine hydrochloride, 2 g of sodium carbonate, and 0.8 g of 9-(2-bromoacetylamino)-4,7-bis-dimethylamino-3,10,12,12a-tetrahydroxy-1,11-dioxo-1,4,4a,5,5a,6,11,12a-octahydronaphthacene-2-carboxylic acid amide in 10 ml DMPU and 3 ml acetonitrile to give 0.315 g of the product.

MS (ESI) m/z 636.3 (M+H);
MS (ESI) m/z 318.7 (M+2H);
HRMS: calcd for $C_{32}H_{37}N_5O_9 \cdot HCl$, 671.2358; found (ESI+), 636.26519;

Example 7

(4S,4aS,5aR,12aS)-4,7-bis(dimethylamino)-3,10,12,12a-tetrahydroxy-9-[(N-methoxy-N-methylglycyl)amino]-1,11-dioxo-1,4,4a,5,5a,6,11,12a-octahydrotetracene-2-carboxamide

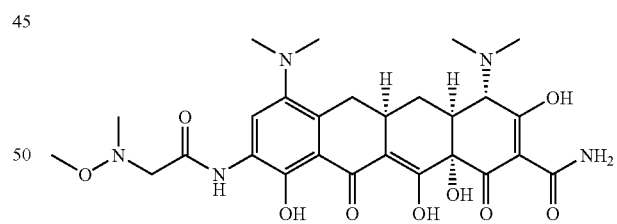

The compound of the example is prepared by the procedure of Example 1 using 10 g of N,O-dimethylhydroxylamine hydrochloride (neutralized by NaOH, extracted with methylene chloride), and 1.0 g of 9-(2-bromo-acetylamino)-4,7-bis-dimethylamino-3,10,12,12a-tetrahydroxy-1,11-dioxo-1,4,4a,5,5a,6,11,12a-octahydro-naphthacene-2-carboxylic acid amide in 8 ml DMPU and 2.5 ml acetonitrile to give 0.495 g of the product.

MS (ESI) m/z 574.3 (M+H);
HRMS: calcd for $C_{27}H_{35}N_5O_9 \cdot HCl$, 609.2202; found (ESI+), 574.24969;

Example 8

(4S,4aS,5aR,12aS)-4,7-bis(dimethylamino)-3,10,12,12a-tetrahydroxy-9-[(1,2-oxazinan-2-ylacetyl)amino]-1,11-dioxo-1,4,4a,5,5a,6,11,12a-octahydrotetracene-2-carboxamide

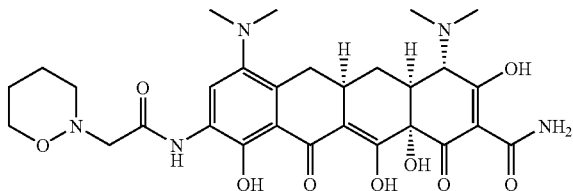

The compound of the example is prepared by the procedure of Example 1 using 2 g of [1,2]oxazinane, and 0.5 g of 9-(2-bromo-acetylamino)-4,7-bis-dimethylamino-3,10,12,12a-tetrahydroxy-1,11-dioxo-1,4,4a,5,5a,6,11,12a-octahydro-naphthacene-2-carboxylic acid amide in 8 ml DMPU and 2 ml acetonitrile to give 0.2 g of the product.

MS (ESI) m/z 600.2 (M+H);
HRMS: calcd for $C_{29}H_{37}N_5O_9 \cdot HCl$, 635.2358; found (ESI+), 600.22614;

Example 9

(4S,4aS,5aR,12aS)-4-(dimethylamino)-3,10,12,12a-tetrahydroxy-7-iodo-9[(1,2-oxazinan-2-ylacetyl)amino]-1,11-dioxo-1,4,4a,5,5a,6,11,12a-octahydrotetracene-2-carboxamide

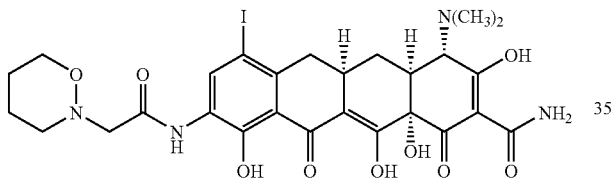

The compound of the example is prepared by the procedure of Example 1 using 1.5 g of [1,2]oxazinane, and 0.3 g of [4S-(4alpha, 12aalpha)]-2-Naphthacenecarboxamide, 9-[(bromoacetyl)amino]-4-(dimethylamino)-1,4,4a,5,5a,6,11,12a-octahydro-3,10,12,12a-tetrahydroxy-7-iodo-1,11-dioxo-, sulfate [J. Med Chem. 37, 184 (1994)] in 5 ml DMPU and 2 ml acetonitrile to give 0.126 g of the product of the example.

MS (ESI) m/z 683.2;
HRMS: calcd for $C_{27}H_{31}IN_4O_9 \cdot HCl$, 718.0903; found (ESI+, [M+H]1+), 683.11931;

The following example is prepared according to scheme 2.

Example 10

(4S,4aS,5aR,12aS)-4-(dimethylamino)-3,10,12,12a-tetrahydroxy-9-[(1,2-oxazinan-2-ylacetyl)amino]-1,11-dioxo-7-thien-2-yl-1,4,4a,5,5a,6,11,12a-octahydrotetracene-2-carboxamide

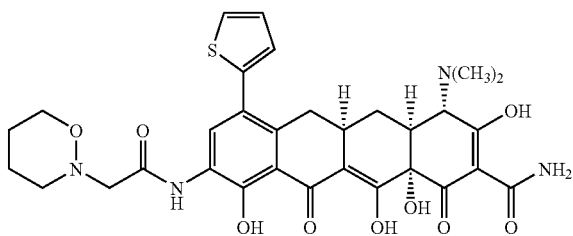

A mixture of 40 mg of Example 9 (4S,4aS,5aR,12aS)-4-(dimethylamino)-3,10,12,12a-tetrahydroxy-7-iodo-9-[(1,2-oxazinan-2-ylacetyl)amino]-1,11-dioxo-1,4,4a,5,5a,6,11,12a-octahydrotetracene-2-carboxamide, 6 mg $Pd(PPh_3)_2Cl_2$ (dichlorobis(triphenyl-phosphine)palladium(II), 2 mg $AsPh_3$, 2 mg CuI (copper(1) iodide) and 2-(tributylstannyl)-thiophene in 10 mL toluene is heated to reflux under nitrogen for ca. 6 h. The reaction mixture is cooled, filtered and solvent removed. The crude residue is dissolved in water at pH 2 (by adding 10% HCl), and 10% ammonium hydroxide is added to adjust the pH to about 4 followed by extraction with methylene chloride. Organic layer dried over sodium sulfate, solvent removed and residue triturated with ether and 1M HCl in ether to give 8 mg of the product of the example.

MS (ESI) m/z 639.3;
HRMS: calcd for $C_{31}H_{34}N_4O_9S \cdot HCl$, 674.1813; found (ESI+, [M+H]1+), 639.21274;

What is claimed is:

1. A compound of Formula (I)

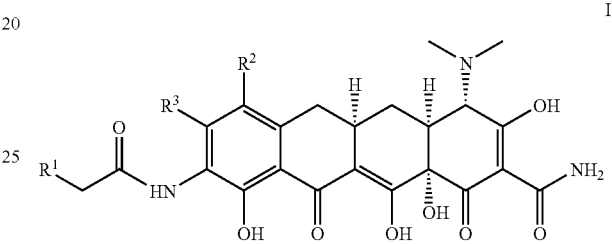

wherein:

$R^1$ is a moiety selected from the group:

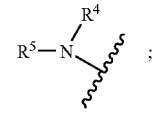

$R^2$ is selected from hydrogen, amino, —$NR^6R^7$, alkyl of 1 to 12 carbon atoms optionally substituted, aryl of 6, 10 or 14 carbon atoms optionally substituted, alkenyl of 2 to 12 carbon atoms optionally substituted, alkynyl of 2 to 12 carbon atoms optionally substituted, halogen, and a 5 to 10 membered heteroaryl ring optionally substituted, having 1 to 4 heteroatoms independently selected from N, O and S;

$R^3$ is selected from hydrogen, alkyl of 1 to 12 carbon atoms optionally substituted, aryl of 6, 10 or 14 carbon atoms optionally substituted, alkenyl of 2 to 12 carbon atoms optionally substituted, vinyl, alkynyl of 2 to 12 carbon atoms optionally substituted and halogen;

$R^4$ is cycloalkyl of 3 to 8 carbon atoms, bicycloalkyl of 5 to 10 carbon atoms or aralkyl optionally substituted;

$R^5$ is —$OR^8$;

$R^6$ and $R^7$ are each independently H or alkyl of 1 to 12 carbon atoms or when optionally taken together with the nitrogen atom to which each is attached form a 3 to 8 membered saturated heterocyclyl ring;

$R^8$ is alkyl of 1 to 12 carbon atoms optionally substituted;

or a tautomer or pharmaceutically acceptable salts thereof.

2. A compound according to claim 1 wherein $R^2$ is a heteroaryl ring of 5 or 6 ring atoms or a pharmaceutically acceptable salt thereof.

3. A compound according to claim 2 wherein $R^2$ is furanyl or a pharmaceutically acceptable salt thereof.

4. A compound according to claim 2 wherein $R^2$ is thienyl or a pharmaceutically acceptable salt thereof.

5. A compound according to claim 1 wherein $R^2$ is pyridinyl or a pharmaceutically acceptable salt thereof.

6. A compound according to claim 1 wherein $R^6$ and $R^7$ are both methyl or a pharmaceutically acceptable salt thereof.

7. A pharmaceutical composition of matter comprising a pharmacologically effective amount of a compound according to claim 1 in association with a pharmaceutically acceptable carrier.

8. A method for the treatment or control of bacterial infections in warm-blooded animals which comprises administering to said animal a pharmacologically effective amount of a compound according to claim 1 or a pharmaceutically acceptable salt thereof.

9. A process for the preparation of a 9-(N-substituted-N-substituted-glycyl) tetracyclines of formula 5

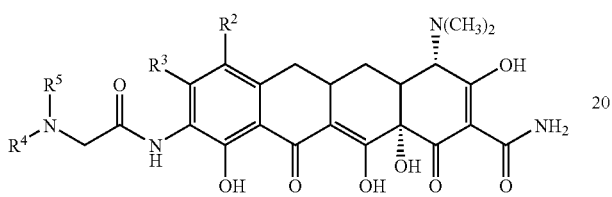

5 wherein:

$R^2$ is selected from hydrogen, amino, —$NR^6R^7$, alkyl of 1 to 12 carbon atoms optionally substituted, aryl of 6, 10 or 14 carbon atoms optionally substituted, alkenyl of 2 to 12 carbon atoms optionally substituted, alkynyl of 2 to 12 carbon atoms optionally substituted, halogen, and a 5 to 10 membered heteroaryl ring optionally substituted, having 1 to 4 heteroatoms independently selected from N, O and S;

$R^3$ is selected from hydrogen, alkyl of 1 to 12 carbon atoms optionally substituted, aryl of 6, 10 or 14 carbon atoms optionally substituted alkenyl of 2 to 12 carbon atoms optionally substituted, vinyl, alkynyl of 2 to 12 carbon atoms optionally substituted and halogen;

$R^4$ is H, alkyl of 1 to 12 carbon atoms optionally substituted, cycloalkyl of 3 to 8 carbon atoms, bicycloalkyl of 5 to 10 carbon atoms or aralkyl optionally substituted;

$R^5$ is $OR^8$;

$R^6$ and $R^7$ are each independently H or alkyl of 1 to 12 carbon atoms or when optionally taken together with the nitrogen atom to which each is attached form a 3 to 8 membered saturated heterocyclyl ring;

$R^8$ is alkyl of 1 to 12 carbon atoms optionally substituted;

or a tautomer or pharmaceutically acceptable salts thereof which comprises reacting haloacetyltetracycline 3

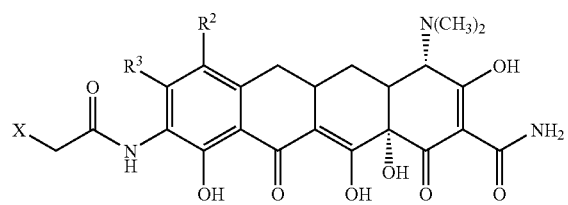

3 with an amine $NHR^4R^5$ in the presence of 1,3-dimethyl-3,4,5,6-tetrahydro-2(1H)-pyrimidinone in an aprotic solvent to afford 9-(N-substituted-N-substituted-glycyl) tetracycline 5.

10. A process for the preparation of a 9-(N-substituted-N-substituted-glycyl) tetracyclines of formula 5

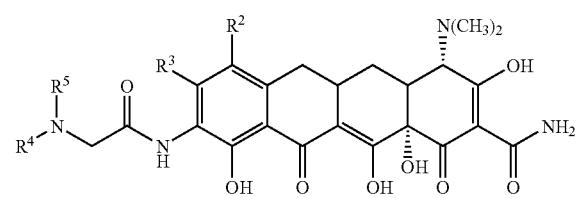

5 wherein:

$R^2$ is selected from hydrogen, amino, —$NR^6R^7$, alkyl of 1 to 12 carbon atoms optionally substituted, aryl of 6, 10 or 14 carbon atoms optionally substituted, alkenyl of 2 to 12 carbon atoms optionally substituted, alkynyl of 2 to 12 carbon atoms optionally substituted, halogen, and a 5 to 10 membered heteroaryl ring optionally substituted, having 1 to 4 heteroatoms independently selected from N, O and S;

$R^3$ is selected from hydrogen, alkyl of 1 to 12 carbon atoms optionally substituted, aryl of 6, 10 or 14 carbon atoms optionally substituted alkenyl of 2 to 12 carbon atoms optionally substituted, vinyl, alkynyl of 2 to 12 carbon atoms optionally substituted and halogen;

$R^4$ is H, alkyl of 1 to 12 carbon atoms optionally substituted, cycloalkyl of 3 to 8 carbon atoms, bicycloalkyl of 5 to 10 carbon atoms or aralkyl optionally substituted;

$R^5$ is $OR^8$;

$R^6$ and $R^7$ are each independently H or alkyl of 1 to 12 carbon atoms or when optionally taken together with the nitrogen atom to which each is attached form a 3 to 8 membered saturated heterocyclyl ring;

$R^8$ is alkyl of 1 to 12 carbon atoms optionally substituted;

or a tautomer or pharmaceutically acceptable salts thereof which process comprises the steps of:

a. reacting a 9-amino-7-substituted-8-substituted-6-demethyl-6-deoxytetracyclines 1 of the formula

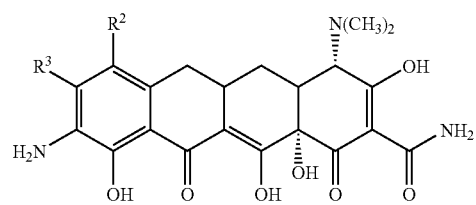

1 with a haloacetyl bromide or chloride 2, where X is bromo or chloro of the formula

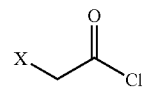

2 to afford a haloacetyltetracycline 3

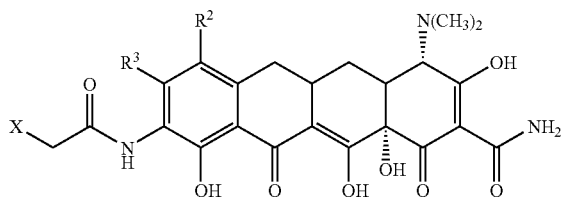

b. reacting haloacetyltetracycline 3 with an amine $NHR^4R^5$ in the presence of 1,3-dimethyl-3,4,5,6-tetrahydro-2(1H)-pyrimidinone in an aprotic solvent to afford 9-(N-substituted-N-substitutedglycyl)tetracycline 5

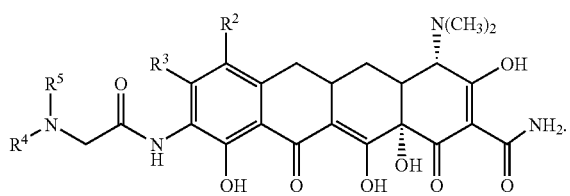

11. A 9-(N-substituted-N-substitutedglycyl)tetracycline of formula 5

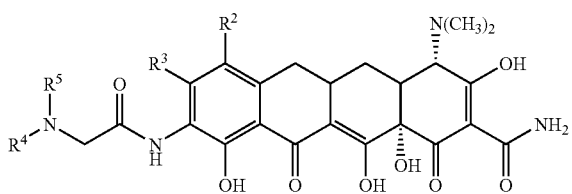

wherein:
$R^2$ is selected from hydrogen, amino, —$NR^6R^7$, alkyl of 1 to 12 carbon atoms optionally substituted, aryl of 6, 10 or 14 carbon atoms optionally substituted, alkenyl of 2 to 12 carbon atoms optionally substituted, alkynyl of 2 to 12 carbon atoms optionally substituted, halogen, and a 5 to 10 membered heteroaryl ring optionally substituted, having 1 to 4 heteroatoms independently selected from N, O and S;
$R^3$ is selected from hydrogen, alkyl of 1 to 12 carbon atoms optionally substituted, aryl of 6, 10 or 14 carbon atoms optionally substituted alkenyl of 2 to 12 carbon atoms optionally substituted, vinyl, alkynyl of 2 to 12 carbon atoms optionally substituted and halogen;
$R^4$ is cycloalkyl of 3 to 8 carbon atoms, bicycloalkyl of 5 to 10 carbon atoms or aralkyl optionally substituted;

$R^5$ is —$OR^8$;
$R^6$ and $R^7$ are each independently H or alkyl of 1 to 12 carbon atoms or when optionally taken together with the nitrogen atom to which each is attached form a 3 to 8 membered saturated heterocyclyl ring;
$R^8$ is alkyl of 1 to 12 carbon atoms optionally substituted;
or a tautomer or pharmaceutically acceptable salts thereof obtainable or produced by the process which comprises the steps of:
a. reacting a 9-amino-7-substituted-8-substituted-6-demethyl-6-deoxytetracyclines 1 of the formula

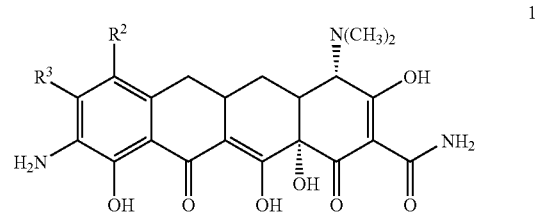

with a haloacetyl bromide or chloride 2, where X is bromo or chloro of the formula

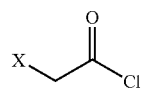

to afford a haloacetyltetracycline 3

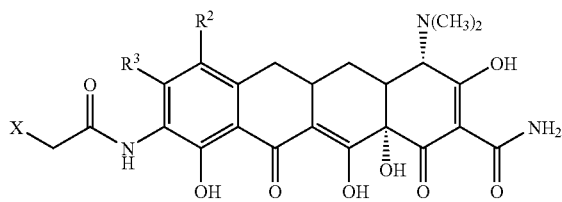

b. reacting haloacetyltetracycline 3 with an amine $NHR^4R^5$ in the presence of 1,3-dimethyl-3,4,5,6-tetrahydro-2(1H)-pyrimidinone in an aprotic solvent to afford 9-(N-substituted-N-substituted glycyl)tetracycline 5

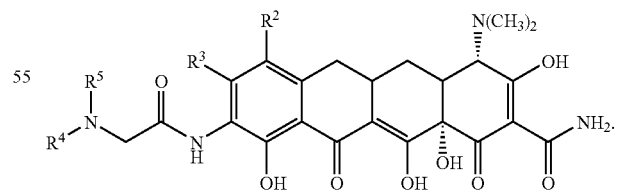

* * * * *